United States Patent [19]

Fillers et al.

[11] Patent Number: 5,100,850
[45] Date of Patent: Mar. 31, 1992

[54] OXIDATIVE SECONDARY RHODIUM RECOVERY PROCESS

[75] Inventors: Carl F. Fillers, Greeneville, Tenn.; Eric D. Middlemas, Nickelsville, Va.; Charles E. Outlaw, Kingsport; Jerry A. Barron, Gray, both of Tenn.

[73] Assignee: Eastman Kodak Company, Rochester, N.Y.

[21] Appl. No.: 695,066

[22] Filed: May 3, 1991

[51] Int. Cl.$^5$ .............. B01J 38/68; B01J 31/40; C22B 11/04; C07C 51/10
[52] U.S. Cl. .............................. 502/24; 423/22; 502/22; 502/28; 502/32; 562/891
[58] Field of Search .............. 502/24, 22, 28, 32; 562/891; 423/22

[56] References Cited

U.S. PATENT DOCUMENTS 4,388,217  6/1983  Hembre et al. .................. 502/28
4,650,649  3/1987  Zoeller ............................ 502/28
4,945,075  7/1990  Cushman et al. ................ 502/24

FOREIGN PATENT DOCUMENTS 0255389  2/1988  European Pat. Off. .......... 502/28
0314352  5/1989  European Pat. Off. .......... 502/24

Primary Examiner—Paul E. Konopka
Attorney, Agent, or Firm—J. Frederick Thomsen; William P. Heath, Jr.

[57] ABSTRACT

Disclosed is an oxidative process for recovering rhodium catalyst values from "tars" formed during the preparation of acetic anhydride by the rhodium catalyzed carbonylation of a mixture of methyl iodide and methyl acetate and/or dimethyl ether. The disclosed process includes the treatment of a tar/methyl iodide solution, which contains rhodium values normally not extracted by aqueous hydrogen iodide, with a solution of hydrogen peroxide and acetic acid.

6 Claims, No Drawings

OXIDATIVE SECONDARY RHODIUM RECOVERY PROCESS

This invention pertains to an oxidative process for recovering rhodium catalyst values from "tars" formed during the preparation of acetic anhydride by the rhodium catalyzed carbonylation of a mixture of methyl iodide and methyl acetate and/or dimethyl ether. More specifically, this invention pertains to an oxidative process for the recovery of rhodium values which normally are not extractable from the tars.

The use of catalyst systems comprising rhodium and an iodine compound in the preparation of acetic anhydride by the carbonylation of methyl acetate has been reported extensively in the patent literature. See, for example, U.S. Pat. Nos. 3,927,078, 4,046,807, 4,374,070 and 4,559,183 and European Patents 8396 and 87,870. These patents disclose that the reaction rate can be increased if the catalyst system includes a promoter such as certain amines, quaternary ammonium compounds, phosphines and inorganic compounds such as lithium compounds.

The formation of tar in carbonylation acetic anhydride processes and the problem of recovering catalyst value therefrom are described in U.S. Pat. No. 4,388,217 and European Patent 255,389. Several processes have been described in the literature for the separation of rhodium from these tars. The majority of these recovery processes involve cumbersome precipitations of the rhodium-containing species and co-catalyst using a variety of organic solvents and an optional subsequent dissolution of he ionic iodide promoters with water. Enriched rhodium-containing material is either returned to the reactor or ashed for the rhodium value. See U.S. Pat. Nos. 4,442,304, 4,440,570, 4,556,644, 4,629,711, 4,746,640, 4,605,541, 4,659,682, and 4,434,240. A simpler variant involving solvent removal, aqueous extraction and ashing is described in U.S. Pat. No. 4,434,241.

U.S Pat. No. 4,434,240 discloses the use of reagents such as alkali metal hydroxides, hydrogen peroxide or its alkali metal salts, and reducing agents, such as sodium borohydride, formaldehyde, and sodium bisulfite to aid in precipitation. The peroxide used in accordance with the disclosed process apparently is consumed in oxidizing iodide ion to elemental iodine.

The handling and transfer of fine, rhodium-containing solids are cumbersome on a commercial scale and liquid phase processes for recovering rhodium catalyst values therefore are preferable in most industrial operations. Several such processes have been described. European Patent Application 250,103 describes a liquid phase electrochemical separation.

A particularly useful liquid phase process for recovering catalyst values is described in U.S. Pat. No. 4,388,217 wherein a catalyst tar solution is submitted to an extraction using methyl iodide and aqueous hydrogen iodide. In the practice of the extraction process, a substantial amount of the rhodium present in the rhodium tar solution is recovered in the aqueous hydrogen iodide phase which may be recycled to the carbonylation process. The presence of the hydrogen iodide in the aqueous phase stabilizes the water soluble rhodium compound or compounds, thereby preventing the loss of insoluble rhodium which can plate out on the extraction equipment and or the walls of pipes, vessels, etc. Most of the tar component of the catalyst tar solution is recovered in the methyl iodide phase.

The above described extraction process generally is very efficient, leaving only small quantities of rhodium in the tar/methyl iodide phase. Since rhodium is extremely expensive, this small portion of rhodium must also be recovered or the acetic anhydride manufacturing process will be subjected to very high catalyst replacement costs. The ashing and recycling involved in recovering these small quantities of rhodium still represents an economic burden on the carbonylation based production of acetic anhydride. Three approaches to recovering the remaining rhodium and iodine present in the tar are described in the patent literature. Two similar processes which involve the precipitation of rhodium in acetic acid are described in U.S. Pat. Nos. 4,578,368 and 4,650,649. These processes suffer the same drawbacks associated with prior precipitation-based processes with the exception that the scale is significantly reduced. A more useful extractive process using aqueous ammonia is described in U.S. Pat. No. 4,364,907. This ammonia based process requires the removal of significant quantities of aqueous ammonia from the rhodium containing solution. The process also introduces small quantities of ammonia into the system which can adversely affect the carbonylation process due to the formation of insoluble tetramethyl ammonium salts.

U.S. Pat. No. 4,945,075 discloses a secondary rhodium recovery process which comprises treating the above mentioned tar/methyl iodide phase with certain oxidants followed by extraction with aqueous hydrogen iodide. The oxidants which may be used include hydrogen peroxide and peracetic acid with the use of the latter being preferred. The use of hydrogen peroxide does not give completely satisfactory results due to its insolubility in the tar/methyl iodide phase whereas peracetic acid involves an additional process step requiring equipment dedicated to its production from acetic acid, hydrogen peroxide and an acid catalyst such as an acidic ion exchange resin which must be replenished or regenerated periodically. The manufacture and storage of peracetic acid on a commercial scale also presents safety problems.

The process provided by this invention involves a secondary, liquid phase treatment of the tars containing rhodium catalyst values, resulting from a methyl iodide/aqueous hydrogen iodide extraction process, e g., the process described in U.S. Pat. No. 4,388,217 discussed above. The process includes the steps of contacting (1) a methyl iodide solution of rhodium containing tar with (2) a solution of hydrogen peroxide and acetic acid. The oxidative treatment of the methyl iodide solution of tars containing rhodium not extracted by the primary methyl iodide/aqueous hydrogen iodide extraction process permits the recovery of 95+% of the previously unextracted rhodium from the tars using a subsequent extraction with aqueous hydrogen iodide. Our novel process is completely compatible with the extraction and carbonylation processes described hereinabove since it does not result in the introduction of any extraneous material to the overall production system. The process is essentially free of solids and is may be operated continuously or semi continuously, especially in conjunction with the described methyl iodide/aqueous hydrogen iodide extraction process.

The process of this invention thus comprises the recovery of rhodium catalyst values from a catalyst-tar solution derived from a production system in which acetic anhydride is prepared by contacting a mixture of methyl acetate and/or dimethyl ether and methyl iodide with carbon monoxide in the presence of a rhodium catalyst comprising the steps of:

(1) submitting the catalyst-tar solution to an extraction with a combination of methyl iodide and aqueous hydrogen iodide and recovering (a) the aqueous phase containing most of the rhodium catalyst values, and (b) the methyl iodide phase containing most of the tar which contains minor amounts of the rhodium catalyst values;

(2) treating the methyl iodide phase of Step (1) with a solution of aqueous hydrogen peroxide and acetic acid; and (3) submitting the treated methyl iodide phase of Step (2) to an extraction with aqueous hydrogen iodide to recover in the aqueous phase rhodium catalyst values present in the treated methyl iodide phase.

The production system from which the catalyst-tar solution referred to above is derived includes systems in which essentially all of the product is acetic anhydride or in which both acetic anhydride and acetic acid are produced in varying ratios. Thus, the mixture fed to the carbonylation reactor may include methanol and/or water in addition to methyl acetate and/or dimethyl ether and methyl iodide.

The amount of the hydrogen peroxide required must exceed the amount which converts the iodide ion ($I^-$) present in the methyl iodide solution of tar to elemental iodine ($I_2$). When all of the iodide ion has been converted to elemental iodine, the oxidative liberation of the previously unextracted rhodium values proceeds quickly. In practice, good results have been achieved by the use of amounts of aqueous hydrogen peroxide which provide about 0.1 to 1.0 moles of hydrogen peroxide ($H_2O_2$) per liter of tar/methyl iodide solution. However, since extraction efficiency of the initial extraction (Step 1 above) can vary significantly in commercial operations, the optimum amount of hydrogen peroxide required also may vary.

The hydrogen peroxide which may be used comprises aqueous hydrogen peroxide having a peroxide content of 3 to 90 weight percent. For economic and safety reasons, the aqueous hydrogen peroxide most suitable for use in the process has a hydrogen peroxide content of about 30 to 70 weight percent, preferably 30 to 40 weight percent.

The tar/methyl iodide solution treated in accordance with my invention may contain from 2 to 20 weight percent tar and from 5 to 50 ppm rhodium, calculated as [Rh], based on the total weight of the tar/methyl iodide solution. More typically, the tar/methyl iodide solution comprises about 5 to 15 weight percent tar and about 5 to 20 ppm rhodium.

The amount of acetic acid employed can be varied substantially depending on other process variables such as the mode of operation and the particular aqueous hydrogen peroxide used. The amount of acetic acid used normally will give a solution of aqueous hydrogen peroxide and acetic acid wherein the aqueous hydrogen peroxide constitutes about 5 to 40, preferably 10 to 30, weight percent of the solution.

In the practice of the process provided by the present invention, the solutions of (1) aqueous hydrogen peroxide and acetic acid, and (2) tar and methyl iodide are fed to an agitated vessel at a rate which provides a residence time of about 15 to 60 minutes. The temperature and pressure maintained within the agitated vessel generally are not critical. Typically, the contacting of the 2 solutions is carried out at ambient pressure and temperatures of about 0 to 45° C.

In a preferred embodiment of the present invention, (i) the methyl iodide phase obtained from the Step (1) extraction, i.e., a solution of rhodium-containing tar in methyl iodide, contains about 5 to 15 weight percent tar, (ii) the solution of aqueous hydrogen peroxide and acetic used to treat the methyl iodide phase contains about 10 to 30 weight percent aqueous hydrogen peroxide having a hydrogen peroxide concentration of about 30 to 40 weight percent, and (iii) the amount of aqueous hydrogen peroxide/acetic acid solution used to treat the methyl iodide phase gives a methyl iodide phase:aqueous hydrogen peroxide/acetic acid solution weight ratio of about 10:1 to 3:1.

The mixture resulting from the treatment of the tar/methyl iodide with the aqueous hydrogen peroxide/acetic acid solution is submitted to an extraction with aqueous hydrogen iodide according to known processes, e.g., the extraction process described in U.S. Pat. No. 4,388,217. The mixture may be fed directly to the process of Step (1), e.g., the extraction process described in Example 12 of U.S. Pat. No. 4,388,217 by adding the mixture to the stripped tar receiver referred to in that Example 12.

Our invention preferably is practiced in a continuous mode of operation comprising the steps of:

I. continuously feeding the catalyst tar solution, methyl iodide and aqueous hydrogen iodide to an extraction vessel;

II. continuously removing from the extraction vessel
 A. an aqueous phase containing most of the rhodium catalyst values; and
 B. a methyl iodide phase containing about 5 to 15 weight percent tar;

III. continuously feeding the methyl iodide phase of Step II.B. to a peroxide treatment vessel;

IV. continuously feeding to the peroxide treatment vessel a solution of aqueous hydrogen peroxide and acetic acid comprising about 10 to 30 weight percent aqueous hydrogen peroxide, preferably having a hydrogen peroxide ($H_2O_2$) content of about 30 to 40 weight percent, wherein the weight ratio of feed III. to feed IV. is about 10:1 to 3:1; and V. continuously removing from the peroxide treatment vessel the peroxide treated mixture and feeding it, directly or indirectly, to the extraction vessel of Step I.

This mode of operation integrates our secondary rhodium recovery process with the continuous operation of the process described in U.S. Pat. No. 4,388,217 embodied by Steps I and II set forth above. It is apparent that the peroxide treated mixture of Step V may be fed to the extraction vessel directly or indirectly by feeding it first to the stripped tar receiver described in Example 12 of U.S. Pat. No. 4,388,217.

The process of the present invention is further illustrated by the following examples. The rhodium-containing, tar/methyl iodide solutions used in the examples were obtained from the extraction process described in U.S. Pat. No. 4,388,217.

EXAMPLES 1-5 AND COMPARATIVE EXAMPLE 1

In each example, a solution consisting of 35% aqueous hydrogen peroxide and, except for Comparative Example 1, acetic acid and a tar/methyl iodide solution were fed continuously to a 500 mL, round-bottom flask fitted with a stirrer. The feed rates provided a hold up or residence time in the flask of 45 minutes except in Example 5 in which the feed rates provided a hold up time of 30 minutes. The contents of the flask were maintained at reflux (40–43° C.) with vigorous stirring. The mixture was overflowed from the 500 Ml flask and collected in a stirred, 1 L, round bottom flask to which a 37% aqueous hydrogen iodide solution was added while maintaining the temperature of the mixture at reflux. After a 30 minute period of vigorous agitation, agitation was discontinued, the aqueous and organic (methyl iodide/tar) phases were allowed to separate and each phase was analyzed for rhodium.

The amounts in grams of the 37% aqueous hydrogen peroxide (Aqueous Peroxide), acetic acid (HOAc) and tar/methyl iodide solution (Tar/MeI) fed per period of hold up time in each of the examples is shown in Table I. Also set forth in Table I is the rhodium concentration in ppm of each tar/methyl iodide solution used and the amount of 47% aqueous hydrogen iodide used in the extraction step of each example. phases and the extraction efficiency achieved in each example is reported in Table II.

TABLE I

| Example | Aqueous Peroxide | HOAc | Tar/MeI Weight | Rh | Aqueous HI |
|---|---|---|---|---|---|
| 1 | 64 | 188 | 1154 | 13.5 | 422 |
| C-1 | 64 | 0 | 1167 | 13.6 | 422 |
| 2 | 64 | 188 | 1172 | 5.1 | 429 |
| 3 | 54 | 500 | 1823 | 11.7 | 660 |
| 4 | 31 | 123 | 1542 | 10.1 | 488 |
| 5 | 69 | 393 | 2312 | 11.4 | 511 |

TABLE II

| Example | Rhodium Concentration Aqueous Phase | Organic Phase | Extraction Efficiency |
|---|---|---|---|
| 1 | 25.8 | 0.6 | 92.8 |
| C-1 | 20.7 | 5.1 | 60.9 |
| 2 | 11.1 | 0.4 | 91.8 |
| 3 | 17.8 | 1.6 | 86.3 |
| 4 | 21.3 | 2.1 | 78.8 |
| 5 | 24.1 | 2.0 | 84.9 |

The advantages provided by the present invention are readily apparent from a comparison of substantially identical Example 1 and Comparative Example 1 (C-1). The extraction efficiency achieved in Example 1 was over 50% greater than that achieved in Comparative Example 1 wherein no acetic acid was used in the peroxide treatment.

The invention has been described in detail with particular reference to preferred embodiments thereof, but it will be understood that variations and modifications may be effected within the spirit and scope of the invention.

We claim:

1. Process for the recovery of rhodium catalyst values from a catalyst tar solution derived from a production system in which acetic anhydride is prepared by contacting a mixture of methyl acetate and/or dimethyl ether and methyl iodide with carbon monoxide in the presence of a rhodium catalyst comprising the steps of:
    (1) submitting the catalyst tar solution to an extraction with a combination of methyl iodide and aqueous hydrogen iodide and recovering (a) the aqueous phase containing most of the rhodium catalyst values, and (b) the methyl iodide phase containing most of the tar which contains minor amounts of the rhodium catalyst values;
    (2) treating the methyl iodide phase of Step (1) with a solution of aqueous hydrogen peroxide and acetic acid; and
    (3) submitting the treated methyl iodide phase of Step (2) to an extraction with aqueous hydrogen iodide to recover in the aqueous phase rhodium catalyst values present in the treated methyl iodide phase.

2. Process according to claim 1 wherein the aqueous hydrogen peroxide constitutes about 5 to 40 weight percent of the solution of aqueous hydrogen peroxide and acetic acid.

3. Process according to claim 2 wherein the amount of the solution of aqueous hydrogen peroxide and acetic acid used to treat the methyl iodide phase provides about 0.1 to 1.0 moles hydrogen peroxide per liter of methyl iodide phase.

4. Process for the recovery of rhodium catalyst values from a catalyst tar solution derived from a production system in which acetic anhydride is prepared by contacting a mixture of methyl acetate and/or dimethyl ether and methyl iodide with carbon monoxide in the presence of a rhodium catalyst comprising the steps of:
    (1) submitting the catalyst tar solution to an extraction with a combination of methyl iodide and aqueous hydrogen iodide and recovering (a) the aqueous phase containing most of the rhodium catalyst values, and (b) the methyl iodide phase containing about 5 to 15 weight percent tar and minor amounts of the rhodium catalyst values;
    (2) treating the methyl iodide phase of Step (1) with a solution of aqueous hydrogen peroxide and acetic acid comprising 10 to 30 weight percent aqueous hydrogen peroxide having a hydrogen peroxide concentration of about 30 to 40 weight percent and the amount of aqueous hydrogen peroxide/acetic acid solution used to treat the methyl iodide phase gives a methyl iodide phase:aqueous hydrogen peroxide/acetic acid solution weight ratio of about 10:1 to 3:1; and
    (3) submitting the treated methyl iodide phase of Step (2) to an extraction with aqueous hydrogen iodide to recover in the aqueous phase rhodium iodide phase.

5. Continuous process for the recovery of rhodium catalyst values from a catalyst tar solution derived from a production system in which acetic anhydride is prepared by contacting a mixture of methyl acetate and/or dimethyl ether and methyl iodide with carbon monoxide in the presence of a rhodium catalyst comprising the steps of:
    I. continuously feeding the catalyst tar solution, methyl iodide and aqueous hydrogen iodide to an extraction vessel;
    II. continuously removing from the extraction vessel
        A. an aqueous phase containing most of the rhodium catalyst values; and
        B. a methyl iodide phase containing about 5 to 15 weight percent tar;
    III. continuously feeding the methyl iodide phase of Step II.B. to a peroxide treatment vessel;
    IV. continuously feeding to the peroxide treatment vessel a solution of aqueous hydrogen peroxide and acetic acid comprising about 10 to 30 weight percent aqueous hydrogen peroxide wherein the weight ratio of feed III. to feed IV. is about 10:1 to 3:1; and V. continuously removing from the peroxide treatment vessel the peroxide treated mixture and feeding it to the extraction vessel of Step I.

6. Process according to claim 5 wherein the aqueous hydrogen peroxide of Step IV has a hydrogen peroxide content of about 30 to 40 weight percent.

* * * * *

UNITED STATES PATENT AND TRADEMARK OFFICE
CERTIFICATE OF CORRECTION

PATENT NO. : 5,100,850

DATED : March 31, 1992

INVENTOR(S) : Carl F. Fillers et al.

It is certified that error appears in the above-identified patent and that said Letters Patent is hereby corrected as shown below:

Column 6, line 47 (Claim 4), between "rhodium" and "iodide" ——catalyst values present in the treated methyl—— should be inserted.

Signed and Sealed this

First Day of June, 1993

Attest:

MICHAEL K. KIRK

Attesting Officer

Acting Commissioner of Patents and Trademarks